(12) United States Patent
Maeda et al.

(10) Patent No.: US 6,495,685 B1
(45) Date of Patent: Dec. 17, 2002

(54) PROCESS FOR PREPARING PIPERAZINE DERIVATIVES

(75) Inventors: Chiharu Maeda; Eiichi Iishi; Weiqi Wang; Yoshiyuki Imamiya, all of Osaka (JP)

(73) Assignee: Sumika Fine Chemicals Co., Ltd., Osaka (JP)

( * ) Notice: Subject to any disclaimer, the term of this patent is extended or adjusted under 35 U.S.C. 154(b) by 0 days.

(21) Appl. No.: 09/697,140

(22) Filed: Oct. 27, 2000

Related U.S. Application Data

(63) Continuation-in-part of application No. PCT/JP00/05432, filed on Aug. 14, 2000.

(30) Foreign Application Priority Data

Sep. 30, 1999 (JP) ............................................. 11-280378

(51) Int. Cl.⁷ ...................... C07C 213/04; C07D 401/04
(52) U.S. Cl. ...................... 544/242; 544/333; 564/363; 564/366
(58) Field of Search ................................. 564/363, 366; 544/333, 242

(56) References Cited

U.S. PATENT DOCUMENTS

| 3,663,548 A | 5/1972 | Nitta et al. ............. 260/268 R |
| 4,025,513 A | 5/1977 | Olivie ..................... 260/251 A |
| 4,062,848 A | 12/1977 | van der Burg ........ 260/268 DC |
| 4,217,452 A | 8/1980 | Olivie ......................... 544/246 |
| 4,772,705 A | 9/1988 | Schmiesing ................. 544/344 |
| 6,339,156 B1 | 1/2002 | Dolitzky ..................... 544/383 |

FOREIGN PATENT DOCUMENTS

| JP | 44-17388 | 7/1969 |
| JP | 5315520 | 5/1978 |
| JP | 5942678 | 10/1984 |
| WO | WO 00/63185 | 10/2000 |

*Primary Examiner*—Richard L. Raymond
(74) *Attorney, Agent, or Firm*—Birch, Stewart, Kolasch & Birch, LLP

(57) ABSTRACT

A process for preparing a piperazine derivative represented by the formula (V):

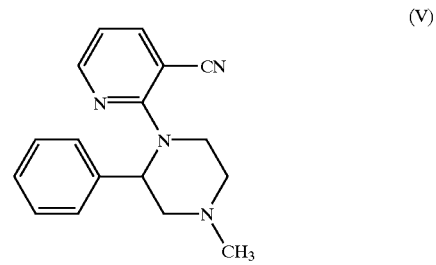

(V)

comprising reacting 1-methyl-3-phenylpiperazine with 2-chloro-3-cyanopyridine in an aprotic polar organic solvent in the presence of a base and an alkali metal halide. The piperazine derivative and its oxalate are compounds useful as preparation intermediates of mirtazapine.

5 Claims, 1 Drawing Sheet

200 μm

PROCESS FOR PREPARING PIPERAZINE DERIVATIVES

This application is a continuation-in-part application of PCT/JP00/05432, filed Aug. 14, 2000 the entire contents of which are incorporated herein by reference.

BACKGROUND OF THE INVENTION

1. Field of the Invention

The present invention relates to a process for preparing piperazine derivatives. More specifically, the present invention relates to a process for preparing piperazine derivatives which can be suitably used as preparation intermediates of mirtazapine, which is useful as an antidepressant.

2. Discussion of the Related Art

Mirtazapine is a compound which is useful as an antidepressant. Conventionally, there have been known piperazine derivatives as preparation intermediates for mirtazapine. As a process for preparing a piperazine derivative, there has been known a process comprising reacting 1-methyl-3-phenylpiperazine with 2-chloro-3-cyanopyridine in the presence of potassium fluoride (Japanese Examined Patent Publication No. Sho 59-42678).

However, since this process uses potassium fluoride, there are some defects in this process that apparatus in which glass is used or apparatus having glass-lining cannot be used in the process because glass is eroded away, and that industrial productivity is poor because tar is generated in the reaction solution in a large amount, thereby making it difficult to take out a desired piperazine derivative.

In addition, as a process for preparing 1-methyl-3-phenylpiperazine, which is an important preparation intermediate for the above-mentioned piperazine derivative, there have been known a process comprising reacting styrene oxide with N-methylethanolamine in water (Japanese Examined Patent Publication No. Sho 53-15520); and a process comprising methylating 2-phenylpiperazine with methyl iodide (U.S. Pat. No. 4,722,705).

However, the former process has some defects in the aspect of productivity because isomers are formed, so that a complicated treatment such as column separation is necessitated. In addition, the latter process has some defects that its industrial productivity is poor because 1-methyl-3-phenylpiperazine cannot be obtained in high yields, and a large amount of acetone is necessitated.

The present invention has been accomplished in view of the prior art described above. An object of the present invention is to provide a process capable of industrially easily preparing piperazine derivatives which are useful as preparation intermediates of mirtazapine, and 1-methyl-3-phenylpiperazine, which is an important preparation intermediate thereof, without requiring complicated procedures. These and other objects of the present invention will be apparent from the following description.

SUMMARY OF THE INVENTION

According to the present invention, there are provided:

(1) a process for preparing a diol compound represented by the formula (I):

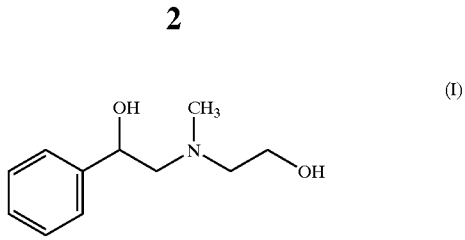

comprising reacting styrene oxide with N-methylethanolamine in an aprotic polar organic solvent;

(2) the process for preparing a diol compound according to item (1) above, wherein the aprotic polar organic solvent is dimethylformamide or 1,3-dimethylimidazolidin-2-one;

(3) a process for preparing a dichloro-compound represented by the formula

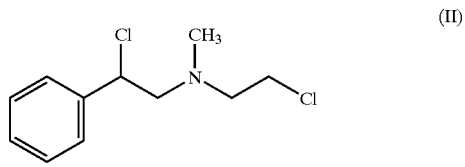

comprising chlorinating the diol compound obtained in item (1) above without isolating the diol compound;

(4) a process for preparing a salt of a dichloro-compound represented by the formula (III):

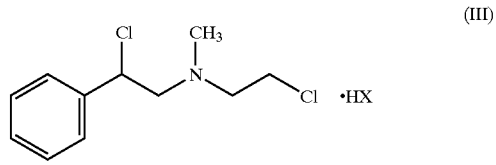

wherein HX is an acid, comprising treating the diol compound obtained in item (1) above with an acid to form a salt, and chlorinating the resulting salt;

(5) a process for preparing 1-methyl-3-phenylpiperazine represented by the formula (IV):

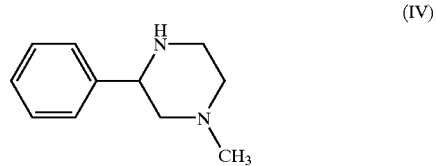

comprising reacting the dichloro-compound obtained in item (3) above or a salt of the dichloro-compound obtained in item (4) above with ammonia;

(6) a process for preparing a piperazine derivative represented by the formula (V):

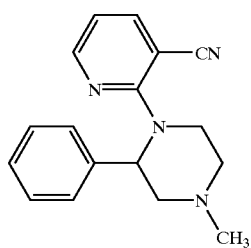

(V)

comprising reacting 1-methyl-3-phenylpiperazine with 2-chloro-3-cyanopyridine in an aprotic polar organic solvent in the presence of a base and an alkali metal halide; and (7) an oxalate of a piperazine derivative represented by the formula (VI):

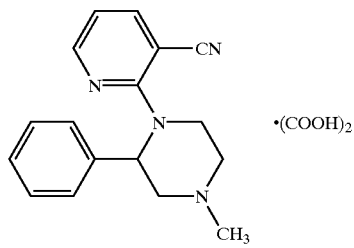

(VI)

DETAILED DESCRIPTION OF THE INVENTION

Figure 1:
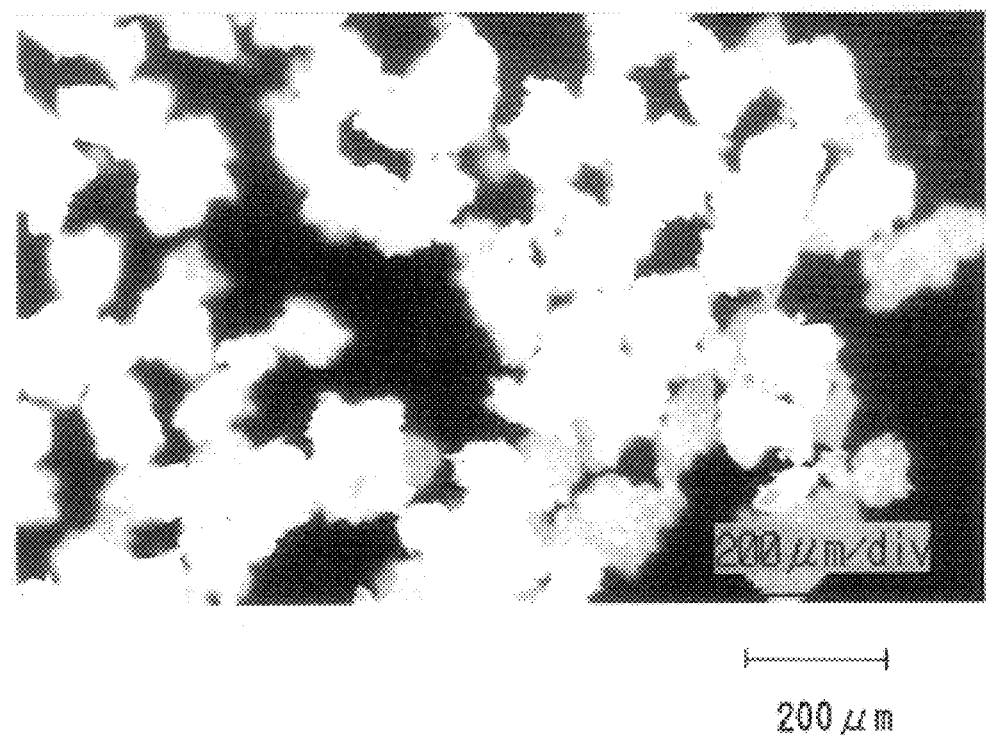
FIG. 1 is a microphotograph of 2-(4-methyl-2-phenylpiperazin-1-yl)-3-cyanopyridine oxalate obtained in Example 11.

First, there can be obtained with excellent selectivity a diol compound represented by the formula (I):

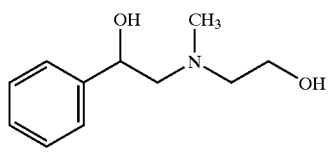

(I)

by reacting styrene oxide with N-methylethanolamine in an aprotic polar organic solvent.

The amount of N-methylethanolamine is not limited to specified ones. In consideration of economics and treatments after the reaction, it is preferable that the amount of N-methylethanolamine is usually 0.8 to 1.2 moles or so per one mole of styrene oxide.

The aprotic polar organic solvent includes, for instance, dimethylformamide, dimethylacetamide, dimethyl sulfoxide, 1,3-dimethylimidazolidin-2-one, N-methyl-2-pyrrolidone, and the like. These aprotic polar organic solvents can be used alone or in admixture of two or more kinds. Among them, dimethylformamide and 1,3-dimethylimidazolidin-2-one can be favorably used in the present invention.

The amount of the aprotic polar organic solvent is not limited to specified ones. It is desired that the amount is usually 100 to 600 parts by volume, preferably 150 to 400 parts by volume, based on 100 parts by weight of styrene oxide.

It is preferable that the reaction is carried out by adding in a thin stream N-methylethanolamine to styrene oxide.

It is desired that the reaction temperature is at least 50° C., preferably at least 70° C., more preferably at least 80° C., from the viewpoint of accelerating the reaction, and that the reaction temperature is at most 120° C., preferably at most 100° C. because a by-product is likely to be formed when the temperature is excessively high.

The atmosphere during the reaction is not limited to specified ones. The atmosphere may be air, or an inert gas, for instance, nitrogen gas.

The reaction time is not limited to specified ones, and it is usually 2 to 5 hours or so. The end point of the reaction can be set at a point, for instance, where the areal percentage of N-methylethanolamine is at most 0.5%, as determined by gas chromatography or the like.

Thus, the diol compound represented by the formula (I) is obtained.

Next, the diol compound is chlorinated, whereby a dichloro-compound can be formed.

It is preferable that the diol compound is formed into a salt prior to chlorination, from the viewpoint of reducing the amount of by-products, thereby readily proceeding with the reaction.

As a process for forming a salt of the diol compound, there can be cited, for instance, a process of introducing an acid [HX in the formula (III)] into a reaction solution containing the formed diol compound. The acid which can be favorably used for forming a salt of the above-mentioned diol compound includes hydrochloric acid (hydrogen chloride gas), hydrobromic acid, methanesulfonic acid, benzenesulfonic acid, p-toluenesulfonic acid, and the like. Among them, hydrochloric acid (hydrogen chloride gas), methanesulfonic acid and benzenesulfonic acid are preferable, and hydrochloric acid (hydrogen chloride gas) and methanesulfonic acid are more preferable.

It is desired that the amount of the acid is at least one equivalent per one equivalent of the diol compound, preferably 1.0 to 1.2 equivalents to the diol compound, in order to sufficiently allow a diol compound to form a salt.

Next, the diol compound or a salt of the diol compound [hereinafter both compounds are collectively referred to as diol compound (salt)] is chlorinated.

When the diol compound is chlorinated with a chlorinating agent such as thionyl chloride, there can be obtained a salt of a dichloro-compound represented by the formula (III):

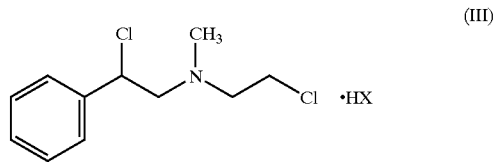

(III)

wherein HX is an acid. In addition, the dichloro-compound represented by the formula (II):

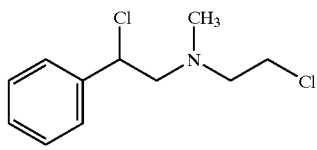

(II)

can be obtained by subjecting a salt of the dichloro-compound obtained to a treatment, for instance, an addition of an alkali or the like.

When the diol compound (salt) is chlorinated, the reaction solution can be directly used, without isolating the diol compound (salt) from the reaction solution containing the diol compound (salt) obtained as described above.

The chlorination of the above-mentioned diol compound (salt) is carried out, for instance, by using a chlorinating agent such as thionyl chloride, phosphorus oxychloride, oxalyl chloride or phosgene. The amount of the chlorinating agent is not limited to specified ones. It is desired that the amount of the chlorinating agent is usually 2 to 3.5 equivalents or so, preferably 2 to 3 equivalents or so per one equivalent of the diol compound (salt).

More specifically, the chlorination of the diol compound (salt) with a chlorinating agent can be easily carried out by, for instance, mixing the chlorinating agent with the reaction solution obtained as described above, and properly stirring the resulting mixture, or alternatively previously dissolving the chlorinating agent in an organic solvent such as toluene, dimethylformamide or 1,3-dimethylimidazolidin-2-one, mixing the organic solvent solution of the chlorinating agent with the reaction solution obtained as described above, and properly stirring the resulting mixture. In this case, it is preferable that the amount of the organic solvent is usually 100 to 500 parts by weight or so, based on 100 parts by weight of the chlorinating agent.

The chlorination of the diol compound (salt) can be easily carried out by adding in a thin stream the diol compound (salt) to a chlorinating agent at 0° to 30° C.

The time period required for the chlorination of the diol compound (salt) is not limited to specified ones, and the time period is usually 1 to 12 hours or so. In addition, the end point of the chlorination can be readily confirmed by, for instance, gas chromatography or the like.

Thus, the diol compound (salt) is chlorinated, to give a dichloro-compound represented by the formula (II) or a salt of a dichloro-compound represented by the formula (III).

In order to remove a chlorinating agent such as thionyl chloride, and a water-soluble organic solvent such as dimethylformamide from the resulting reaction solution containing the dichloro-compound or salt of the dichloro-compound, for instance, the reaction solution is firstly added in a thin stream to water. It is preferable that the amount of water is usually 100 to 300 parts by weight, based on 100 parts by weight of the water-soluble organic solvent such as dimethylformamide. It is desired that the dropping temperature is usually 0° to 30° C., preferably 0° to 25° C.

Next, an aqueous alkali is added in a thin stream to the reaction solution to adjust its pH to 0.8 to 1.0. As the aqueous alkali, there can be used an aqueous potassium hydroxide or aqueous sodium hydroxide in a concentration of 10 to 40% by weight. It is desired that the dropping temperature is 0° to 25° C., preferably 0° to 20° C. It is preferable that the aqueous alkali is previously cooled to 5° to 10° C.

Next, an aqueous alkali is added to the above-mentioned reaction solution so that the pH of the reaction solution can be adjusted to 4 to 5. It is preferable that the aqueous alkali is introduced thereto at a temperature of 0° to 25° C.

It is desired that the resulting mixture is extracted with an ether solvent such as diisopropyl ether, an ester solvent such as ethyl acetate or butyl acetate, or a hydrocarbon solvent such as toluene, and preferably with toluene. In addition, as occasion demands, the dichloro-compound can be isolated by washing the extract, drying it over anhydrous magnesium sulfate, anhydrous sodium sulfate or the like, adding activated clay or the like thereto, and thereafter filtering the mixture.

When the dichloro-compound is isolated as a salt, 30 to 100 parts by weight of isopropanol based on 100 parts by weight of N-methylethanolamine used, is added to the resulting filtrate, and thereafter hydrogen chloride may be introduced thereinto. It is preferable that the amount of hydrogen chloride is 0.9 to 1.2 moles or so, per one mole of the N-methylethanolamine used. When hydrogen chloride is added, it is preferable that hydrogen chloride is added once after cooling the reaction solution to a temperature of 20° C. or less, since the reaction involves heat generation.

The crystals of a salt of the dichloro-compound having excellent filtering ability can be obtained by stirring this solution or allowing this solution to stand at 10°) to 20° C. for 1 to 2 days.

Next, 1-methyl-3-phenylpiperazine represented by the formula (IV):

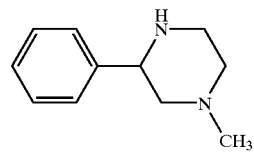

(IV)

can be obtained by reacting the resulting dichloro-compound represented by the formula (II), or the resulting salt of the dichloro-compound represented by the formula (III), with ammonia.

The reaction of the dichloro-compound or the salt of the dichloro-compound [hereinafter referred to as dichloro-compound (salt)] with ammonia can be carried out, for instance, in a solvent.

As the solvent, there can be favorably used, for instance, at least one solvent selected from aprotic polar organic solvents such as dimethylformamide; hydrocarbon solvents such as toluene; ester solvents such as ethyl acetate and butyl acetate; and ether solvents such as diisopropyl ether. Among them, a mixed solvent of dimethylformamide and toluene is preferable. It is desired that the amount of the solvent is usually 100 to 1000 parts by volume, preferably 120 to 800 parts by volume, based on 100 parts by weight of the dichloro-compound (salt).

Ammonia may be blown into the solvent directly in a gaseous state, or it may be dissolved in water to be used as an aqueous ammonia. When ammonia is used as an aqueous ammonia, it is preferable that the concentration of ammonia in the aqueous ammonia is usually 15 to 28% or so. It is desired that the amount of ammonia is 10 to 50 moles, preferably 15 to 30 moles, more preferably 20 to 30 moles, per one mole of the dichloro-compound (salt), from the viewpoints of reactivity and economics.

In addition, when the dichloro-compound (salt) is reacted with ammonia, it is preferable to use a quaternary ammonium salt from the viewpoint of accelerating the reaction by phase transfer. The quaternary ammonium salt includes, for instance, tetrabutylammonium bromide, benzyltrimethylammonium chloride, benzyltrimethylammonium bromide, benzyltriethylammonium chloride, benzyltriethylammonium bromide, tricaprylmethylammonium chloride, tetrabutylammonium iodide, and the like. These quaternary ammonium salts can be used alone or in admixture of two or more kinds. It is desired that the amount of the quaternary ammonium salt is 200 mg to 50 g, preferably 200 mg to 30 g, more preferably 1 to 30 g, per one mole of the dichloro-compound (salt), from the viewpoints of reactivity and economics.

The temperature during the reaction of the dichloro-compound (salt) with ammonia is not limited to specified ones, and it is desired that the temperature is usually 10° to 80° C., preferably 20° to 50° C., more preferably 30° to 50° C.

The reaction time is not limited to specified ones, and it is usually 1 to 10 hours or so. In addition, the end point of the reaction can be readily confirmed by, for instance, high-performance liquid chromatography, gas chromatography, or the like.

An aqueous alkali such as sodium hydroxide is added to a reaction solution containing the 1-methyl-3-phenylpiperazine represented by the formula (IV) thus obtained to make the solution alkaline. It is preferable that the concentration of the aqueous alkali is 20 to 50% by weight or so. In addition, the reaction solution may be alkaline, for instance, its pH can be 11 to 12 or so.

Next, 1-methyl-3-phenylpiperazine can be isolated by a process comprising, for instance, extracting the solution which is made alkaline at least once with toluene, ethyl acetate, an ether or the like, preferably toluene, drying the extract over anhydrous magnesium sulfate or the like, and thereafter distilling the dried extract.

The preparation of 2-(4-methyl-2-phenylpiperizin-1-yl)-3-cyanopyridine from 1-methyl-3-phenylpiperazine can be readily carried out by, for instance, reacting 1-methyl-3-phenylpiperazine with 2-chloro-3-cyanopyridine in an aprotic polar organic solvent in the presence of a base and an alkali metal halide.

It is desired that the amount of 1-methyl-3-phenylpiperazine is 0.7 to 1.1 moles, preferably 0.8 to 1.1 moles, more preferably 0.8 to 1.0 moles, per one mole of 2-chloro-3-cyanopyridine, from the viewpoint of sufficiently progressing the reaction with 2-chloro-3-cyanopyridine.

In the course of the reaction of the two components, an aprotic polar organic solvent is used. As the aprotic polar organic solvent, there can be cited dimethylformamide, dimethylacetamide, dimethyl sulfoxide, 1,3-dimethylimidazolidin-2-one, and the like. Among them, dimethylformamide can be favorably used. The amount of the solvent is not limited to specified ones, and it is desired that the amount of the solvent is usually 100 to 800 parts by volume, preferably 150 to 500 parts by volume, based on 100 parts by weight of 1-methyl-3-phenylpiperazine.

In addition, during the reaction, a base is used in order to accelerate the reaction and inhibit the formation of by-products. As the base, there can be cited organic bases including alkylamines such as triethylamine and diisopropylethylamine; cyclic amines such as N-methylmorpholine; and arylamines such as pyridine and picoline; and inorganic bases such as potassium carbonate and sodium carbonate. It is desired that the amount of the base is 0.5 to 20 moles, preferably 0.7 to 2 moles, per one mole of 2-chloro-3-cyanopyridine, from the viewpoint of rapidly progressing the reaction of 1-methyl-3-phenylpiperazine with 2-chloro-3-cyanopyridine.

In addition, in the present invention, an alkali metal halide is used in order to accelerate the reaction. The alkali metal halide includes potassium iodide, sodium iodide, and the like. It is desired that the amount of the alkali metal halide is 0.05 to 1.5 moles, preferably 0.07 to 1.2 moles, per one mole of 2-chloro-3-cyanopyridine, from the viewpoints of its dissolubility and economics.

Incidentally, in the present invention, as a catalyst, there may be used a quaternary ammonium salt, for instance, tetrabutylammonium iodide, tetrabutylammonium bromide, benzyltrimethylammonium chloride, or the like in a proper amount.

It is preferable that the reaction of 1-methyl-3-phenylpiperazine with 2-chloro-3-cyanopyridine is carried out in an inert gas, for instance, nitrogen gas, argon gas, or the like.

In addition, it is desired that the reaction temperature is usually 90° to 160° C., preferably 110° to 150° C., from the viewpoints of improving the reaction rate and suppressing the formation of by-products. Although the reaction time cannot be absolutely determined because it differs depending upon the reaction temperature, the reaction time is usually 12 to 24 hours.

In addition, the reaction may be carried out under the reaction conditions such that the reaction mixture is refluxed at a reaction temperature of 110° to 125° C. for 8 to 12 hours, a low-volatile distillation fraction is distilled off at 125° to 135° C., and then the remaining mixture is heated at 135° to 140° C. for 5 to 10 hours.

After the termination of the reaction of 1-methyl-3-phenylpiperazine with 2-chloro-3-cyanopyridine, there can be readily isolated 2-(4-methyl-2-phenylpiperazin-1-yl)-3-cyanopyridine, which is a piperazine derivative represented by the formula (V):

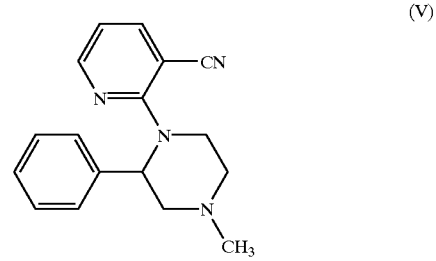

by concentrating the solvents contained in the resulting reaction solution, or alternatively by adding water, extracting with a solvent such as ethyl acetate, and concentrating the extract to obtain crude product; and re-crystallizing from an appropriate solvent.

For instance, 75 to 95% of dimethylformamide used is distilled off from the reaction solution at an internal temperature of 70° to 95° C. under a reduced pressure of 7 to 2.7 kPa, and 100 to 250 parts by weight of water based on 100 parts by weight of 1-methyl-3-phenylpiperazine is added thereto at 70° to 80° C.

Next, its pH is adjusted to 8 to 9 with an alkali. The alkali includes sodium hydroxide, sodium carbonate, and the like. When sodium hydroxide is used as the alkali, it can be usually employed as a 10 to 40% by weight aqueous sodium hydroxide.

Next, this reaction solution is extracted with ethyl acetate. It is preferable that the amount of ethyl acetate is 300 to 1500 parts by weight, based on 100 parts by weight of 1-methyl-3-phenylpiperazine. In addition, it is preferable that the extraction temperature is 40° to 50° C.

In the present invention, there can be used as a piperazine derivative a salt of 2-(4-methyl-2-phenylpiperazin-1-yl)-3- cyanopyridine formed by dissolving the resulting 2-(4-methyl-2-phenylpiperazin-1-yl)-3-cyanopyridine in an organic solvent such as ethyl acetate, methanol or ethanol; adding an acid to the resulting solution; filtering the mixture; and drying the resulting residue. In this case, as the acid, there can be used, for instance, organic acids such as oxalic acid, succinic acid, maleic acid, methanesulfonic acid and toluenesulfonic acid; and inorganic acids such as sulfuric acid, hydrochloric acid and phosphoric acid. Among them, oxalic acid is preferable from the viewpoints of crystallinity, purity and yield.

For instance, to the solution containing 2-(4-methyl-2-phenylpiperazin-1-yl)-3-cyanopyridine extracted from the reaction solution may be added 100 to 150 parts by weight of methanol based on 100 parts by weight of 1-methyl-3-phenylpiperazine, and thereafter added oxalic acid dihydrate at 40° to 50° C., or alternatively may be added in a thin stream a solution prepared by dissolving oxalic acid in methanol in a proportion of 250 to 400 parts by weight of methanol based on 100 parts by weight of oxalic acid. It is preferable that the amount of oxalic acid is 0.9 to 1.5 moles, per one mole of 1-methyl-3-phenylpiperazine.

Next, this solution can be cooled to 15° to 25° C., aged for 1 to 10 hours, and thereafter filtered, and the residue can be washed with a mixed solvent of methanol and ethyl acetate (for instance, 3 to 4 parts by volume of ethyl acetate, based on 1 part by volume of methanol). Thereafter, an oxalate of a piperazine derivative represented by the formula (VI):

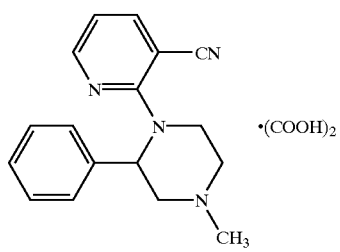

(VI)

can be obtained by drying the resulting compound at a drying temperature of 50° to 60° C.

The piperazine derivative and an oxalate of the piperazine derivative thus obtained are useful compounds as preparation intermediates of mirtazapine.

EXAMPLES

Next, the present invention will be described more specifically on the basis of the examples, without intending to limit the present invention thereto.

Example 1

Preparation of Diol Compound 20 kg (166 moles) of styrene oxide was added to 38 kg of dimethylformamide, and 11.4 kg (151 moles) of N-methylethanolamine was added in a thin stream to the resulting mixture at about 80° C. Thereafter, the resulting mixture was stirred at 80° C. for 3 hours, and the termination point of the reaction was confirmed by gas chromatography. The reaction mixture was cooled to room temperature, to give a dimethylformamide solution of a diol compound.

It could be confirmed that the resulting diol compound was N-(2-hydroxyethyl)-N-methyl-α-hydroxy-β-phenylethylamine from the finding that the resulting diol compound had the following physical properties. $^1$H-NMR (400 MHz, CDCl$_3$) δ ppm: 7.26–7.37 (m, 5H), 4.73–4.77 (m, 1H), 3.66–3.67 (m, 2H), 3.0–4.0 (m, 4H), 2.5–2.7 (m, 4H), 2.37 (s, 3H)

Example 2

Preparation of Methanesulfonate of Diol Compound

To 50 ml of dimethylformamide was added 25 g (0.2 moles) of styrene oxide, and 14.3 g (0.19 moles) of N-methylethanolamine was added in a thin stream to the resulting mixture at 80° C. The mixture was stirred at 80° C. for 3 hours, and the termination point of the reaction was confirmed by gas chromatography. The reaction mixture was then cooled.

Next, 85 g of toluene was added to the resulting reaction mixture. The mixture was cooled to 10° C., and 18.2 g of methanesulfonic acid was added in a thin stream thereto.

A part of the resulting solution was concentrated under reduced pressure, and the concentrate was analyzed. As a result, it was confirmed that the compound was N-(2-hydroxyethyl)-N-methyl-α-hydroxy-β-phenylethylamine methanesulfonate from the following results.

$^1$H-NMR (400 MHz, DMSO-d$_6$) δ ppm: 9.20 (1H, OH), 7.3–7.7 (m, 6H), 5.08 (m, 1H, C$\underline{H}$O), 3.2–3.4 (m, 4H, 2×C$\underline{H}_2$N), 2.92 (dd-like, 3H, NCH$_3$), 2.37 (d-like, 3H, C$\underline{H}_3$SO)

Example 3

Preparation of Hydrochloride Salt of Dichloro-Compound

To the reaction mixture obtained in Example 2 was added in a thin stream 56.2 g (0.19 moles) of thionyl chloride at 0° to 30° C., and the resulting mixture was stirred at 20° to 30° C. for 6 hours. The reaction mixture was cooled, and thereafter added in a thin stream to 120 ml of water at a temperature of 18° to 24° C.

Next, 225 g of a 30% aqueous potassium hydroxide was added in a thin stream to the resulting mixture at a temperature of 20° to 25° C. to adjust its pH to 4.4. The mixture was allowed to stand to separate into two layers.

Six grams of anhydrous magnesium sulfate was added to the organic layer, and the mixture was stirred for 10 minutes. Six grams of activated clay was added, and the mixture was stirred for 15 minutes. Thereafter, the mixture was filtered and washed with 21.7 g of toluene. Sixty grams of a 11.6% ethyl acetate solution of hydrogen chloride (0.19 moles) was added in a thin stream at 28° to 38° C. to the toluene solution, and the mixture was stirred at 20° to 30° C. for one hour. The mixture was filtered, and the resulting residue was washed with 87 g of toluene and dried at 45° to 60° C., to give 37.7 g of hydrochloride of N-(2-chloroethyl)-N-methyl-α-chloro-β-phenylethylamine (hydrochloride of a dichloro-compound) (yield: 73.9%).

Example 4

Preparation of Dichloro-Compound

With adjusting the temperature of the reaction mixture prepared in the same manner as in Example 1 to 0° to 25° C., the reaction mixture was added in a thin stream to a solution prepared by dissolving 45 kg of thionyl chloride in 67.4 kg of toluene. Thereafter, the mixture was stirred at 45° to 55° C. for 2 hours.

The resulting reaction mixture was cooled to a temperature of at most 25° C., and thereafter 95 kg of water was added in a thin stream to the cooled reaction mixture. Subsequently, 50.8 kg of a 30% by weight aqueous potassium hydroxide was added in a thin stream to the resulting mixture at 20° to 25° C. The mixture was allowed to stand to separate into two layers.

Fifty-five kilograms of toluene was added to the obtained aqueous layer, and the mixture was stirred and allowed to separate into two layers. The extracted organic layer was combined with the previously collected organic layer, and the combined organic layer was dehydrated over 4.8 kg of anhydrous magnesium sulfate. Thereafter, 4.8 kg of activated clay was added to the resulting mixture, and the mixture was filtered, and the residue was subsequently washed with 19.9 kg of toluene, to give a toluene solution of a dichloro-compound.

Example 5

Preparation of Salt of Dichloro-Compound

To the toluene solution obtained in Example 4 was introduced 5.5 kg of hydrogen chloride gas at 10° to 35° C. The mixture was stirred at 20° to 25° C. for 2 hours, and the residue was washed with 69 kg of toluene, to give 30 kg of a product.

It was confirmed that the resulting product was a dichloro-compound [N-(2-chloroethyl)-N-methyl-α-chloro-β-phenylethylamine] hydrochloride from the finding that the resulting product had the following physical properties.

$^1$H-NMR (400 MHz, DMSO-$d_6$) δ ppm: 7.397–7.766 (m, 5H), 5.82 (bd, 1H), 3.41–4.1 (m, 6H), 2.908 (s, 3H) Melting point: 123.8° to 126.7° C.

Example 6

Preparation of 1-Methyl-3-Phenylpiperazine

To 132 g (2.175 moles) of a 28% aqueous ammonia were added 100 ml of ethyl acetate, 460 mg of tetrabutylammonium bromide and 20.1 g (0.075 moles) of hydrochloride of the dichloro-compound obtained in Example 3 at room temperature. The resulting mixture was stirred at 40° to 45° C. for 3 hours.

The resulting reaction mixture was allowed to separate into two layers, and the aqueous layer was extracted twice with 30 ml of ethyl acetate at 40° to 45° C., and the collected organic layers were combined together. Thereafter, the combined organic layer was distilled under reduced pressure, to give 7.1 g of a product (yield based on hydrochloride of the dichloro-compound: 53.8%).

It was confirmed that the resulting compound was 1-methyl-3-phenylpiperazine from the finding that the resulting product had the following physical properties.

$^1$H-NMR (400 MHz, CDCl$_3$) δ ppm: 1.8–1.9 (br, 1H), 1.95–2.19 (m, 2H), 2.31 (s, 3H), 2.78–3.15 (m, 4H), 3.84–3.89 (m, 1H), 7.22–7.41 (m, 5H) Boiling point (400 Pa): 107° to 112° C.

Example 7

Preparation of Piperazine Derivative

To 11 ml of dimethylformamide were added 5.51 g (31.3 mmol) of 1-methyl-3-phenylpiperazine obtained in Example 6, 4.47 g (31.3 mmol) of 2-chloro-3-cyanopyridine, 4.1 g (31.3 mmol) of triethylamine and 5.20 g (31.3 mmol) of potassium iodide, and the resulting mixture was reacted at 125° to 130° C. for 24 hours in nitrogen gas atmosphere.

Next, triethylamine and dimethylformamide were distilled off from the reaction mixture under reduced pressure, and thereafter 20 ml of water and 25 ml of ethyl acetate were added to the resulting mixture. The pH of the reaction mixture was adjusted to 8 to 9 with a 10% aqueous sodium hydroxide. The mixture was allowed to separate into two layers. Thereafter, the aqueous layer was extracted twice with 30 ml of ethyl acetate, and the organic layers were combined together. The combined organic layer was washed with 5% aqueous sodium hydrogencarbonate.

The organic layer was dried over anhydrous magnesium sulfate and concentrated. The residue was crystallized from petroleum ether, to give 3.14 g of pale yellow 2-(4-methyl-2-phenylpiperazin-1-yl)-3-cyanopyridine (yield based on 1-methyl-3-phenylpiperazine: 36%, melting point: 65.7° to 66.8° C.). Its HPLC purity was 97.1%.

Example 8

Preparation of Piperazine Derivative

To 11 ml of dimethylformamide were added 5.51 g (31.3 mmol) of 1-methyl-3-phenylpiperazine obtained in Example 6, 4.47 g (31.3 mmol) of 2-chloro-3-cyanopyridine, 4.1 g (31.3 mmol) of triethylamine and 5.20 g (31.3 mmol) of potassium iodide, and the resulting mixture was reacted at 125° to 130° C. for 24 hours in nitrogen gas atmosphere.

Next, triethylamine and dimethylformamide were distilled off under reduced pressure from the reaction mixture, and thereafter 20 ml of water and 25 ml of ethyl acetate were added to the mixture. The pH of the reaction mixture was adjusted to 8 to 9 with a 10% aqueous sodium hydroxide. The mixture was allowed to separate into two layers. Thereafter, the aqueous layer was extracted twice with 30 ml of ethyl acetate, and the organic layers were combined together. The combined organic layer was washed with 5% aqueous sodium hydrogencarbonate.

The organic layer was dried over anhydrous magnesium sulfate, and thereafter a solution prepared by dissolving 3.9 g of oxalic acid in 15 ml of methanol was added to the organic layer.

Next, the solution was filtered, and dried, to give 6.8 g of a white product (yield based on 1-methyl-3-phenylpiperazine: 59%). Its HPLC purity was 99.2%. It was confirmed that the resulting product was 2-(4-methyl-2-phenylpiperazin-1-yl)-3-cyanopyridine oxalate from the finding that the resulting product had the following physical properties.

$^1$H-NMR (CDCl$_3$, 400 MHz) δ ppm: 8.29, 7.77, 6.76 (dd, each 1H); 7.1–7.44 (m, 5H); 5.46 (t, 1H, C$\underline{H}$Ph); 3.83, 3.59 (m, each H); 2.95 (dd, 1H); 2.65–2.80 (m, 4H); 2.55 (m, 1H); 2.33 (s, 3H, NC$\underline{H}_3$)

Example 9

Preparation of Diol Compound to Dichloro-Compound

A reactor was charged with 296.3 kg (2466 moles) of styrene oxide and 559 kg of dimethylformamide, and 169.3 kg (2254 moles) of N-methylethanolamine was added in a thin stream to the resulting mixture at 75° to 84° C. The mixture was stirred at the same temperature for 2 hours. The termination point of the reaction was confirmed by gas chromatography. As a result, N-methylethanolamine was not detected.

Next, the solution was cooled to 10° C., and the solution was added in a thin stream to a mixed solution of 930.3 kg of toluene and 667 kg (5606 moles) of thionyl chloride at 0° to 23° C.

A vessel in which the liquid mixture had been placed was washed with 70.8 kg of toluene, and the resulting washing liquid was added to the reaction mixture. The mixture was stirred at 45° to 52° C. for 2 hours. The mixture was analyzed by gas chromatography. As a result, it was confirmed that N-(2-hydroxyethyl)-N-methyl-α-hydroxy-β-phenylethylamine disappeared. The reaction mixture was cooled to about 10° C., and added in a thin stream at 20 to 29° C. to 998 kg of water to hydrolyze excess thionyl chloride.

The reactor was washed with 105.3 kg of toluene, and the washing liquid was added to the hydrolyzed solution. A 25% aqueous sodium hydroxide was added in a thin stream thereto at 3° to 19° C. until pH was attained to 1, and a 25% aqueous sodium hydroxide (1073 kg) was further added at 6° to 25° C. until pH was attained to 4.2. Its organic layer was separated therefrom, and the aqueous layer was extracted with 711 kg of toluene, and the organic layers were combined. The combined organic layer was dehydrated over 70.7 kg of anhydrous magnesium sulfate, and 71.4 kg of activated clay (commercially available from Mizusawa Kagaku K. K. under the trade name of V2) was added thereto to decolorize the organic layer. Thereafter, the organic layer was filtered.

The filtered residue was washed with 254.9 kg of toluene, and 94.3 kg of isopropanol was added to the filtrate. Therethrough was blown at 20° C. 81.2 kg of hydrogen chloride gas, and the reaction mixture was aged for one day, and filtered. The resulting crystals were washed with 692 kg of toluene. The amount of wet crystals was 524.3 kg. As a result of analysis, 409.9 kg of N-(2-chloroethyl)-N-methyl-α-chloro-β-phenylethylamine hydrochloride (hydrochloride of the dichloro-compound) was contained in the wet crystals (yield based on N-methylethanolamine: 67.7%).

Example 10

Preparation of 1-Methyl-3-Phenylpiperazine

A reactor was charged with 515 kg of toluene, 1320 kg of dimethylformamide, 41 kg of tetrabutylammonium bromide and 1392 kg of a 28% aqueous ammonia. A slurry mixture of 524.3 kg (pure content: 409.9 kg) of the wet crystals of N-(2-chloroethyl)-N-methyl-α-chloro-β-phenylethylamine hydrochloride obtained in Example 9 and 519.2 kg of toluene was introduced thereinto. A vessel in which the slurry mixture had been placed was washed with 178 kg of toluene, and the washing liquid was introduced into the reactor. The mixture was stirred at 40° to 44° C. for 2 hours, and the termination point of the reaction was confirmed by gas chromatography. A solution prepared by dissolving 109 kg of sodium hydroxide in 246.3 kg of a 25% aqueous sodium hydroxide was added thereto to adjust its pH to 11.7. The mixture was stirred at 45° to 47° C. for 2 hours, and allowed to separate into layers. To the aqueous layer was added a solution prepared by dissolving 31 kg of sodium hydroxide in 71 kg of a 25% aqueous sodium hydroxide, and the resulting mixture was stirred and extracted at 23° to 24° C. with 461 kg of toluene. Further, 461 kg of toluene was added to the aqueous layer with stirring to extract. The organic layers were combined, and the combined organic layer was dried over 76 kg of anhydrous magnesium sulfate. The organic layer was filtered, and the filtered residue was washed with 143 kg of toluene. The filtrate was concentrated under reduced pressure to distill off toluene. Further, dimethylformamide was distilled off under reduced pressure (450 to 720 Pa), and thereafter, 157.8 g of 1-methyl-3-phenylpiperazine was obtained as a main component (yield: 58.7%). Its boiling point was from 98° to 122° C. (0.2 to 2 kPa).

Incidentally, since the distillated 1-methyl-3-phenylpiperazine solidifies at room temperature, it is preferable that this compound is dissolved in dimethylformamide which is used in the subsequent process.

Example 11

Preparation of Piperazine Derivative

A reactor was charged with 284.6 kg of dimethylformamide, 150.9 kg of 1-methyl-3-phenylpiperazine obtained in Example 10, 14.2 kg of potassium iodide, 142.3 kg of 2-chloro-3-cyanopyridine and 91 kg of triethylamine, and the mixture was heated. The mixture was stirred at 115° to 120° C. for 10 hours, and thereafter the mixture was heated until the internal temperature reached 135° C. to distill off triethylamine.

Further, the mixture was stirred at 135° to 137° C. for 5 hours. The termination point of the reaction was confirmed by HPLC, and thereafter the mixture was cooled to 80° C. Two-hundred and fifty kilograms of dimethylformamide was distilled off at the internal temperature of 300 to 79° C. under reduced pressure of 6.5 to 2.7 kPa. Thereinto was introduced 226.3 kg of water, and 35 kg of a 25% aqueous sodium hydroxide was added at 41° C. to adjust its pH to 8.2. Thereto was added 612.3 kg of ethyl acetate at 41° C. with stirring to extract, and the mixture was allowed to stand to separate into layers. The organic layer was washed with 5% brine, and the washed organic layer was allowed to stand at 47° C. to separate into layers. One-hundred and seventy-nine kilograms of methanol was introduced into the organic layer, and 107.9 kg of oxalic acid dihydrate was added in divided portions at 41° to 49° C. The mixture was stirred at 43° to 49° C. for 1 hour, cooled to 18° to 20° C., and aged for 80 minutes, and thereafter the mixture was filtered. The filtration speed was 2685 L/hr.

The resulting crystals were washed with a mixed solvent of 164.3 kg of ethyl acetate and 47.85 kg of methanol, and the crystals were dried at 50° to 60° C. under reduced pressure, to give 195.3 kg of 2-(4-methyl-2-phenylpiperazin-1-yl)-3-cyanopyridine oxalate (yield: 61.9%). Its HPLC purity was 99.4%, and its melting point was 200° to 210° C., and its bulk density was 0.4 g/mL.

The microphotograph of the resulting 2-(4-methyl-2-phenylpiperazin-1-yl)-3-cyanopyridine oxalate is shown in FIG. 1. In addition, its physical properties are as follows.

IR (KBr)ν=3039, 2223, 1733, 1636, 1578, 1567, 1436, 758, 701 cm$^{-1}$ $^1$H-NMR (CDCl$_3$, 400 MHz) δ ppm: 8.29, 7.77, 6.76 (dd, each 1H); 7.1–7.44 (m, 5H), 5.46 (t, 1H, C$\underline{H}$Ph); 3.83, 3.59 (m, each H); 2.95 (dd, 1H); 2.65–2.80 (m, 4H); 2.55 (m, 1H); 2.33 (s, 3H NC$\underline{H}_3$)

Comparative Example 1

In 28 mL of dimethylformamide were dissolved 2.0 g of 1-methyl-3-phenylpiperazine and 1.62 g of 2-chloro-3-cyanopyridine. Thereto was added 1.92 g of dry potassium fluoride under nitrogen atmosphere. The resulting mixture was stirred at 135° to 140° C.

After 4 hours passed, the reaction was monitored by HPLC. As a result, it was found that the production yield of the desired 2-(4-methyl-2-phenylpiperazin-1-yl)-3-cyanopyridine was 66.5%. Further, the reaction was proceeded for additional 2 hours, and it was found that the production yield became 50.7%. Since impurities were increased, the reaction was ceased.

The resulting reaction mixture was poured into 150 mL of water, and extracted with 100 mL of ethyl acetate. The organic layer was washed with 30 mL of water, and dried over anhydrous magnesium sulfate. Thereafter, the organic layer was concentrated. Although an attempt for crystallization was made with a solvent such as hexane, the mixture did not crystallize.

Therefore, the organic layer was purified by silica gel column chromatography, to give 1.58 g of 2-(4-methyl-2-phenylpiperazin-1-yl)-3-cyanopyridine (yield: 50.3%). Its melting point was 66.2° C.

The 1-methyl-3-phenylpiperazine obtained by the process of the present invention can be favorably used as piperazine derivatives, which are used as preparation intermediates of mirtazapine, and preparation intermediates thereof.

EQUIVALENT

Those skilled in the art will recognize, or be able to ascertain using simple routine experimentation, many equivalents to the specific embodiments of the invention described in the present specification. Such equivalents are intended to be encompassed in the scope of the present invention as recited in the following claims.

What is claimed is:

1. A process for preparing a diol compound represented by the formula (I):

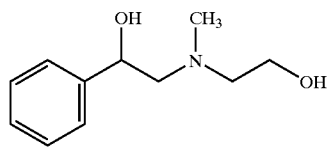

(I)

comprising reacting styrene oxide with N-methylethanolamine in an aprotic polar organic solvent selected from dimethylformamide and 1,3-dimethylimidazolidin-2-one.

2. A process for preparing a dichloro-compound represented by the formula (II):

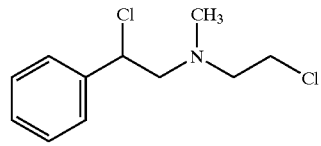

(II)

comprising chlorinating the diol compound obtained in claim 1 without isolating the diol compound.

3. A process for preparing 1-methyl-3-phenylpiperazine represented by the formula (IV):

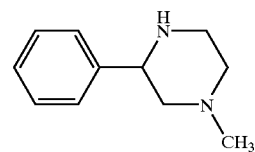

(IV)

comprising reacting the dichloro-compound obtained in claim 2 with ammonia.

4. A process for preparing a piperazine derivative represented by the formula (V):

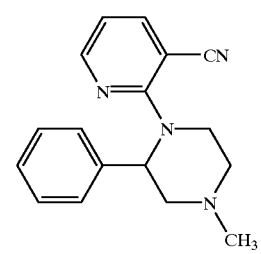

(V)

comprising reacting 1-methyl-3-phenylpiperazine with 2-chloro-3-cyanopyridine in an aprotic polar organic solvent in the presence of (a) an organic base and (b) potassium iodide or sodium iodide.

5. An oxalate of a piperazine derivative represented by the formula (VI):

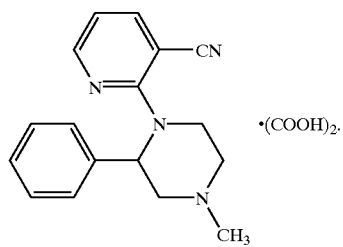

(VI)

* * * * *